US012089969B2

(12) United States Patent
McSweeney et al.

(10) Patent No.: US 12,089,969 B2
(45) Date of Patent: Sep. 17, 2024

(54) PERSONALIZED ALARM SETTINGS

(71) Applicant: Welch Allyn, Inc., Skaneateles Falls, NY (US)

(72) Inventors: WonKyung McSweeney, Manlius, NY (US); Alexandre Hernandez Froio, Syracuse, NY (US); Christopher L. Long, Chittenango, NY (US)

(73) Assignee: Welch Allyn, Inc., Skaneateles Falls, NY (US)

( * ) Notice: Subject to any disclaimer, the term of this patent is extended or adjusted under 35 U.S.C. 154(b) by 43 days.

(21) Appl. No.: 18/065,384

(22) Filed: Dec. 13, 2022

(65) Prior Publication Data

US 2023/0190209 A1  Jun. 22, 2023

Related U.S. Application Data

(60) Provisional application No. 63/265,714, filed on Dec. 20, 2021.

(51) Int. Cl.
*A61B 5/00* (2006.01)
*G08B 21/18* (2006.01)

(52) U.S. Cl.
CPC .............. *A61B 5/746* (2013.01); *A61B 5/721* (2013.01); *G08B 21/182* (2013.01); *A61B 5/6892* (2013.01)

(58) Field of Classification Search
CPC ....... A61B 5/746; A61B 5/721; A61B 5/6892; G08B 21/182
USPC .................................................... 340/539.12
See application file for complete search history.

(56) References Cited

U.S. PATENT DOCUMENTS

| | | | |
|---|---|---|---|
| 8,594,776 B2* | 11/2013 | McCombie | A61B 5/721 600/595 |
| 9,901,261 B2 | 2/2018 | Mccombie et al. | |
| 10,299,734 B2 | 5/2019 | Watson et al. | |
| 10,413,254 B2* | 9/2019 | Sarkela | G16H 40/67 |
| 10,765,320 B1 | 9/2020 | Miller et al. | |
| 11,004,322 B2* | 5/2021 | Pekarske | A61B 5/746 |
| 11,475,751 B1* | 10/2022 | Lee | A61B 5/7282 |
| 2011/0245688 A1* | 10/2011 | Arora | A61B 5/0205 600/595 |
| 2015/0126822 A1 | 5/2015 | Chavan et al. | |
| 2016/0163187 A1* | 6/2016 | Treacy | A61B 5/7282 340/501 |
| 2016/0165380 A1* | 6/2016 | Kwan | H04W 4/80 455/41.1 |
| 2017/0257844 A1* | 9/2017 | Miller | H04M 1/72454 |
| 2018/0008207 A1* | 1/2018 | Sarkela | G16H 40/67 |
| 2018/0140231 A1 | 5/2018 | Kubo et al. | |
| 2018/0353115 A1* | 12/2018 | Cronin | A61B 5/746 |
| 2019/0142343 A1* | 5/2019 | Emmons | A61B 5/349 600/301 |
| 2020/0027328 A1* | 1/2020 | Pekarske | A61B 5/721 |
| 2020/0214566 A1* | 7/2020 | Allen | A61B 5/749 |
| 2021/0020278 A1 | 1/2021 | Chahal et al. | |

(Continued)

*Primary Examiner* — Zhen Y Wu
(74) *Attorney, Agent, or Firm* — Merchant & Gould P.C.

(57) ABSTRACT

A method for monitoring a patient includes detecting a personal device of the patient, sending an invitation to connect to the personal device, and receiving health data from the personal device when the invitation is accepted. The method further includes determining stabilized values for one or more physiological variables of the patient based on the health data, and adjusting one or more alarm settings based on the stabilized values.

15 Claims, 4 Drawing Sheets

(56) References Cited

U.S. PATENT DOCUMENTS

| | | |
|---|---|---|
| 2021/0052170 A1 | 2/2021 | Stewart |
| 2021/0052221 A1 | 2/2021 | Panneer Selvam et al. |
| 2023/0299806 A1* | 9/2023 | Hao .................. H04W 12/50 |
| | | 455/569.1 |

* cited by examiner

PERSONALIZED ALARM SETTINGS

BACKGROUND

Often when a patient is admitted to a healthcare facility such as a hospital, the patient is not at his or her normal stable state. For example, his or her vitals may be elevated or altered due to the condition that brought the patient to the healthcare facility for treatment. This can lead to alarm settings that are not properly set for the patient, and which can result in false alarms.

SUMMARY

In general terms, the present disclosure relates to a monitoring device that receives health data from wearable smart devices worn by a patient over a period of time prior to admission to a healthcare facility, and that uses the health data to determine a normal resting state for the patient to personalize one or more alarm settings for the patient. Various aspects are described in this disclosure, which include, but are not limited to, the following aspects.

One aspect relates to a device for monitoring a patient, comprising: at least one processing device; and a memory device storing instructions which, when executed by the at least one processing device, cause the device to: detect a personal device of the patient; send an invitation to connect to the personal device; receive health data from the personal device when the invitation is accepted; determine stabilized values for physiological variables of the patient based on the health data; and adjust one or more alarm settings based on the stabilized values.

Another aspect relates to a method for monitoring a patient, the method comprising: detecting a personal device of the patient; sending an invitation to connect to the personal device; receiving health data from the personal device when the invitation is accepted; determining stabilized values for one or more physiological variables of the patient based on the health data; and adjusting one or more alarm settings based on the stabilized values.

Another aspect relates to a non-transitory computer readable storage medium storing instructions, which when executed by at least one processing device, cause the at least one processing device to: detect a personal device of the patient; send an invitation to connect to the personal device; when the invitation is accepted, receive health data from the personal device; determine stabilized values for one or more physiological variables of the patient based on the health data; and adjust one or more alarm settings based on the stabilized values.

DESCRIPTION OF THE FIGURES

The following drawing figures, which form a part of this application, are illustrative of the described technology and are not meant to limit the scope of the disclosure in any manner.

DETAILED DESCRIPTION

Figure 1:
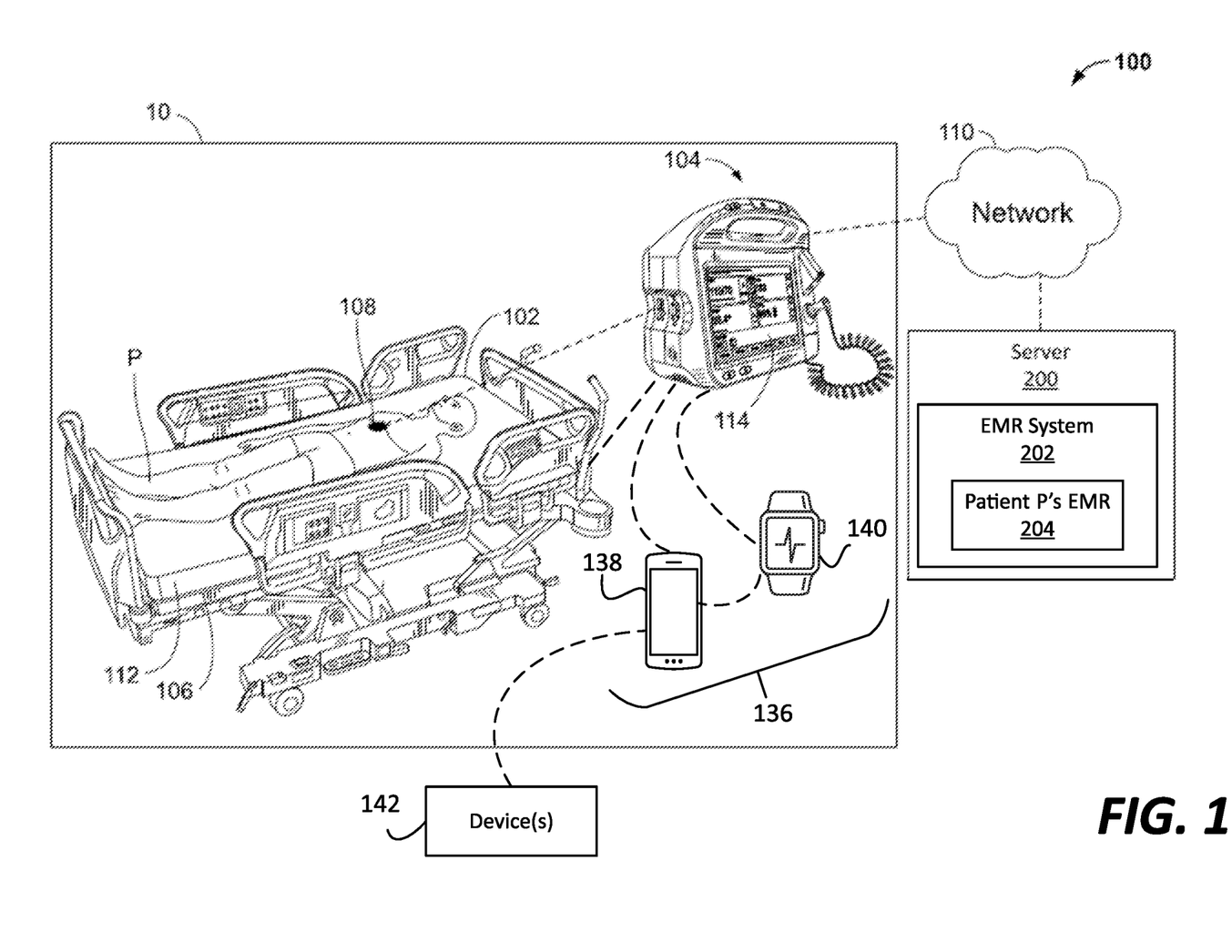
FIG. 1 illustrates an example of a system including a monitor device for monitoring physiological variables of a patient resting on a patient support system.

FIG. 1 illustrates an example of a system 100 for monitoring physiological variables of a patient P who is shown resting on a patient support system 102. The system 100 includes the patient support system 102, as well as a monitor device 104, a motion sensor 106, and one or more physiological sensors 108, which are all shown inside an area 10. In some examples, the area 10 is a patient room, a mid-acuity or low-acuity environment, a pre-operative or post-operative holding area, an operating room, a waiting room, or other type of area within a healthcare facility such as a hospital, a surgical center, a nursing home, a long term care facility, or similar type of facility. In further examples, the area 10 can be the patient P's home.

The patient P is a person, such as a patient, who is being clinically treated by one or more clinicians in the area 10. Examples of clinicians include primary care providers (e.g., doctors, nurse practitioners, and physician assistants), nursing care providers (e.g., nurses), specialty care providers (e.g., professionals in various specialties), and health professionals that provide preventive, curative, promotional and rehabilitative health care services.

In the example shown in FIG. 1, the patient support system 102 is a hospital bed. In other examples, the patient support system 102 is another type of bed, lift, chair, wheelchair, stretcher, surgical table, and the like, which can support the patient P in the area 10.

As shown in FIG. 1, the patient support system 102 is communicatively connected to the monitor device 104 through a wireless or wired link. The patient support system 102 includes a frame that supports a mattress 112, and siderails that are coupled to the frame.

The monitor device 104 is an example of an integrator device that receives data from source devices such as the patient support system 102, the motion sensor 106, and the one or more physiological sensors 108. The monitor device 104 includes a computing device 120 (shown in FIG. 2) that processes the data from the source devices to make decisions such as whether to delay, suppress, or trigger one or more alarms. The monitor device 104 includes a display device 114 for displaying the data acquired from the source devices including the patient support system 102, the motion sensor 106, and the one or more physiological sensors 108.

The monitor device 104 may be any suitable type of monitoring device. In the example provided in FIG. 1, the monitor device 104 is illustrated as a multi-parameter device which displays on the display device 114 multiple parameters detected from the source devices. In alternative examples, the monitor device 104 can be a single-parameter device.

The monitor device 104 can accommodate various alarm features for monitored physiological variables such as traditional alarm thresholds (e.g., upper and lower alarm limits), traditional alarm delays, weighted alarm delays, multivariate index alarms, and the like. In certain examples, the monitor device 104 is a spot monitor, and may include the features described in U.S. Pat. No. 9,265,429, which is herein incorporated by reference in its entirety.

The system 100 can include a plurality of the physiological sensors 108 for monitoring multiple physiological variables. In some examples, a physiological sensor 108 is a multiparameter sensor that can measure multiple physiological variables as a single device.

Examples of the one or more physiological sensors 108 include an electrocardiogram (ECG) sensor, a pulse oximeter sensor that measures blood oxygen saturation (SpO2), a blood pressure sensor for measuring both systolic and diastolic blood pressure, a heart rate sensor, a respiration rate sensor, an end tidal carbon dioxide (etCO2) sensor that can also be used to measure integrated pulmonary index (IPI), a temperature sensor, and the like. The one or more physiological sensors 108 can also combine two or more sensors into a single sensor device.

As shown in FIG. 1, the monitor device 104 communicates with a server 200 via a communications network 110. The server 200 operates to manage the patient P's medical history and information. The server 200 can be operated by a healthcare service provider, such as a hospital or medical clinic. The monitor device 104 sends physiological data acquired from the source devices to the server 200 via the connection to the communications network 110. In at least some examples, the server 200 is a cloud server or similar type of server.

The server 200 can include an electronic medical record (EMR) system 202 (alternatively termed electronic health record (EHR)). Advantageously, the server 200 can automatically store the physiological data acquired from the monitor device 104 in an electronic medical record 204 or electronic health record of the patient P located in the EMR system 202 via the connection with the monitor device 104 over the communications network 110.

In the example shown in FIG. 1, the motion sensor 106 is a motion sensor positioned below, within, or on top of a mattress 112 of the patient support system 102. The motion sensor 106 can include piezoelectric sensors, load cells, or combinations thereof that detect movements of the patient P while the patient P is supported on the patient support system 102.

In some examples, the motion sensor 106 may be an accelerometer attached to the patient P, or incorporated into a physiological sensor 108 and/or into one or more other sensing devices that are attached to the patient P. In such examples, physiological sensing and motion detection functions are combined in one device. Multiple such devices may be used on the patient P. For example, a combined ECG/motion detection device and/or a combined respiration rate/motion detection device may be used on the patient P at the same time.

The motion sensor 106 detects motion by the patient P, which can affect or influence the heart rate, blood pressure, and respiration rate data sensed by the one or more physiological sensors 108. The motion sensor 106 senses motion by the patient P (e.g., by using piezoelectric or load cell sensors positioned below, within, or on top of a mattress 112 or accelerometers attached to the patient P), and transmits the sensed motion data to the monitor device 104 while the one or more physiological sensors 108 sense physiological data such as the heart rate, blood pressure, or respiration rate, and transmit the physiological data to the monitor device 104.

The communications network 110 can include any type of wired or wireless connections or any combinations thereof. Examples of wireless connections include cellular network connections such as 4G or 5G. Wireless connections can also be accomplished using Wi-Fi, ultra-wideband (UWB), Bluetooth, and similar types of wireless connections.

The communications network 110 can communicate data between one or more devices such as between the monitor device 104 and the server 200. The communications network 110 can also be used to communication data between one or more devices inside the area 10 such as between one or more of the patient support system 102, the monitor device 104, the motion sensor 106, the physiological sensors 108, and other devices.

As further shown in FIG. 1, the monitor device 104 can connect to one or more personal devices 136 that belong to the patient P. The personal devices 136 store health data of the patient P that is monitored and tracked prior to the patient P's admission to the area 10.

In the example illustrated in FIG. 1, the one or more personal devices 136 include a mobile device 138 and a fitness tracker 140. In this example, the monitor device 104 can connect to the mobile device 138 and/or the fitness tracker 140. Examples of the mobile device 138 can include a smartphone, a tablet computer, and similar portable computing devices. As an illustrative example, the fitness tracker 140 can include a wearable device such as a smartwatch that syncs with the mobile device 138 (e.g., wirelessly through Bluetooth).

FIG. 1 shows the personal devices 136 as including both the mobile device 138 and the fitness tracker 140. In alternative examples, the personal devices 136 can include only the mobile device 138 or only the fitness tracker 140. Also, the personal devices 136 can include additional types of devices that can measure and/or record relevant health data of the patient P.

As shown in FIG. 1, the monitor device 104 can connect to either or both of the personal devices 136 by using a wireless connection such as Wi-Fi, ultra-wideband (UWB), Bluetooth, and similar types of wireless connections. In some instances, the monitor device 104 can connect to the personal devices 136 through the communications network 110.

The fitness tracker 140 is an example of a wearable device (e.g., smartwatch) worn by the patient P for monitoring health data such as distance walked or run, calorie consumption, and one or more physiological variables. Examples of the one or more physiological variables can include physiological variables that are continuously monitored by the fitness tracker 140 while being worn by the patient P such as, without limitation, heart rate, electrocardiogram (ECG), blood oxygen saturation (SpO2), respiration rate, temperature, and the like. In some instances, the mobile device 138 can also monitor and track health data such as distance walked or run, calorie consumption, and one or more physiological variables by itself without having to sync with another personal device such as the fitness tracker 140.

The mobile device 138 when synced with the fitness tracker 140 can receive the health data for visualization and long-term data tracking. In some examples, the health data received from the fitness tracker 140 is stored on a memory device of the mobile device 138. In some further examples, the health data received from the fitness tracker 140 is stored on a cloud server and is accessible for viewing on the mobile device 138 and/or on the fitness tracker 140.

As further shown in FIG. 1, the mobile device 138 can sync with personal healthcare devices 142 that are outside of the area 10 (e.g., in the patient P's home). Illustrative examples of the personal healthcare devices 142 can include a blood glucose monitor, a blood pressure monitor, and a smart scale. The mobile device 138 can sync with the personal healthcare devices 142 using a wireless connection such as Wi-Fi, ultra-wideband (UWB), Bluetooth, and similar types of wireless connections when the mobile device 138 is in close proximity to the personal healthcare devices 142 prior to the patient P's admission to the area 10 for receiving and/or storing health data of the patient P. In some instances, the mobile device 138 can connect to the personal healthcare devices 142 through the communications network 110.

The mobile device 138 can receive health data from the personal healthcare devices 142. For example, the mobile device 138 can receive, store, or otherwise have access to health data (e.g., via a cloud server) from a blood glucose monitor for monitoring blood glucose levels of the patient P when the patient P is at home (e.g., prior to admission to the area 10).

As another example, the mobile device 138 can receive, store, or otherwise have access to health data (e.g., via a cloud server) from a blood pressure monitor that measures systolic and diastolic blood pressure and cardiac health metrics (e.g., ECG, heart rate, and the like) of the patient P when the patient P is at home (e.g., prior to admission to the area 10).

As another example, the mobile device 138 can receive, store, or otherwise have access (e.g., via a cloud server) to health data from a smart scale that measures weight, body mass index (BMI), full body composition (body fat and water percentage, plus muscle and bone mass), and the like when the patient P is at home (e.g., prior to admission to the area 10). Additional examples of smart devices with which the mobile device 138 can sync with to receive, store, or otherwise have access to health data are contemplated.

Figure 2:
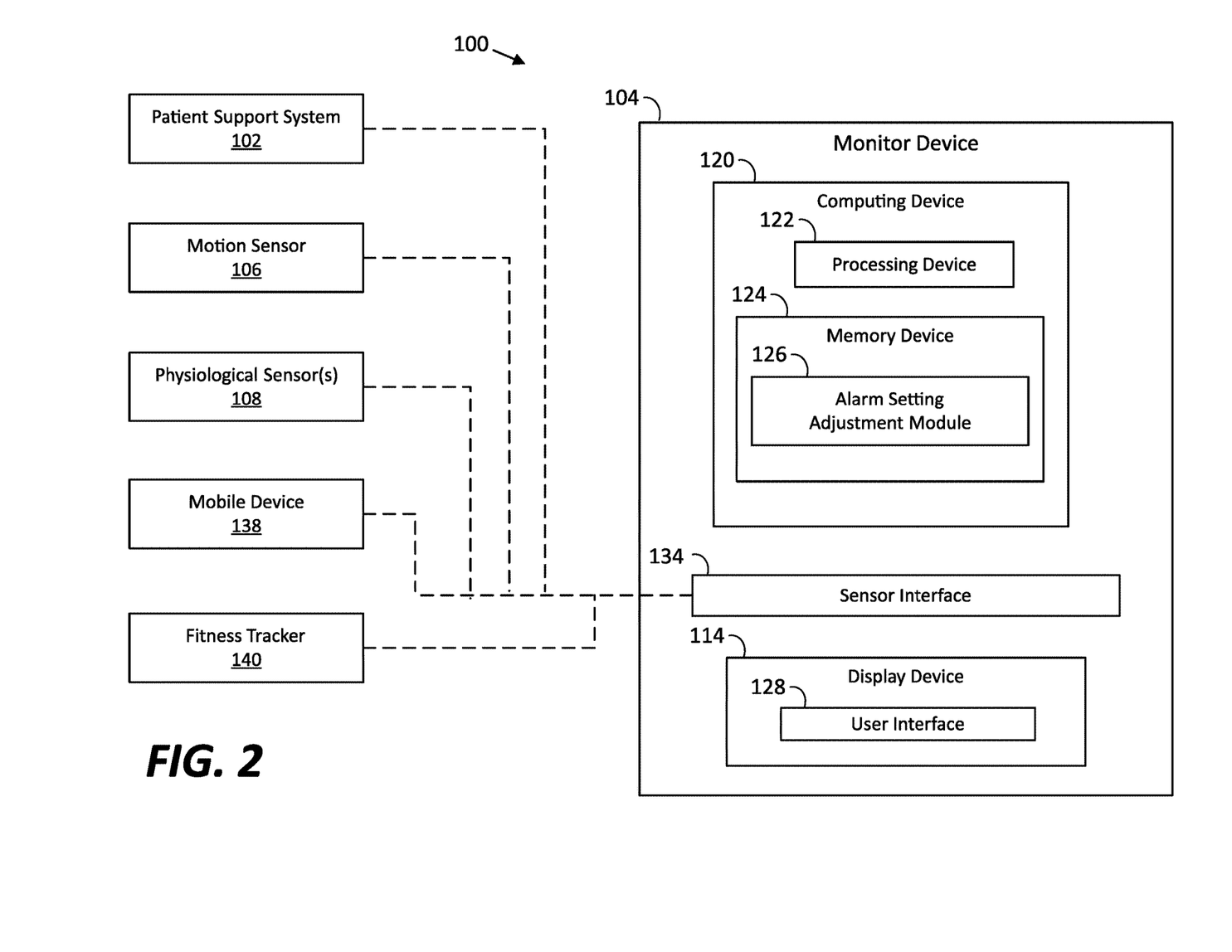
FIG. 2 schematically illustrates an example of the system of FIG. 1, which includes various source devices connected to the monitor device.

FIG. 2 schematically illustrates an example of the system 100. As shown in FIG. 2, the monitor device 104 includes a computing device 120 having a processing device 122 and a memory device 124. The processing device 122 is an example of a processing unit such as a central processing unit (CPU). The processing device 122 can include one or more central processing units (CPU). In some examples, the processing device 122 can include one or more digital signal processors, field-programmable gate arrays, or other electronic circuits.

The memory device 124 operates to store data and instructions for execution by the processing device 122. The memory device 124 includes computer-readable media, which may include any media that can be accessed by the monitor device 104. By way of illustrative example, computer-readable media include computer readable storage media and computer readable communication media. In the example illustrated in FIG. 2, the memory device 124 stores an alarm setting adjustment module 126, which will be described in more detail below.

Computer readable storage media includes volatile and nonvolatile, removable and non-removable media implemented in any device configured to store information such as computer readable instructions, data structures, program modules, or other data. Computer readable storage media can include, but is not limited to, random access memory, read only memory, electrically erasable programmable read only memory, flash memory, and other memory technology, including any medium that can be used to store information that can be accessed by the monitor device 104. The computer readable storage media is non-transitory.

Computer readable communication media embodies computer readable instructions, data structures, program modules or other data in a modulated data signal such as a carrier wave or other transport mechanism and includes any information delivery media. The term "modulated data signal" refers to a signal that has one or more of its characteristics set or changed in such a manner as to encode information in the signal. By way of example, computer readable communication media includes wired media such as a wired network or direct-wired connection, and wireless media such as acoustic, radio frequency, infrared, and other wireless media. Combinations of any of the above are within the scope of computer readable media.

The monitor device 104 includes a sensor interface 134 that operates to communicate with various source devices such as the patient support system 102, the motion sensor 106, the one or more physiological sensors 108, the mobile device 138, and the fitness tracker 140. Additional examples of source devices can include infusion pumps, ventilators, and the like.

The sensor interface 134 can include both wired interfaces and wireless interfaces. For example, the source devices can wirelessly connect to the sensor interface 134 through Wi-Fi, ultra-wideband (UWB), Bluetooth, and similar types of wireless connections. In further examples, the source devices can connect to the monitor device 104 using wired connections that can plug into one or more sockets or receptacles of the sensor interface 134.

As shown in FIG. 2, the monitor device 104 includes the display device 114, which operates to display a user interface 128. In some examples, the display device 114 is a touchscreen such that the user interface 128 operates to receive inputs from a clinician. In such examples, the display device 114 operates as both a display device and a user input device. The monitor device 104 can also support physical buttons on a housing of the device that operate to receive inputs from the clinician to control operation of the monitor device and enter data.

Figure 3:
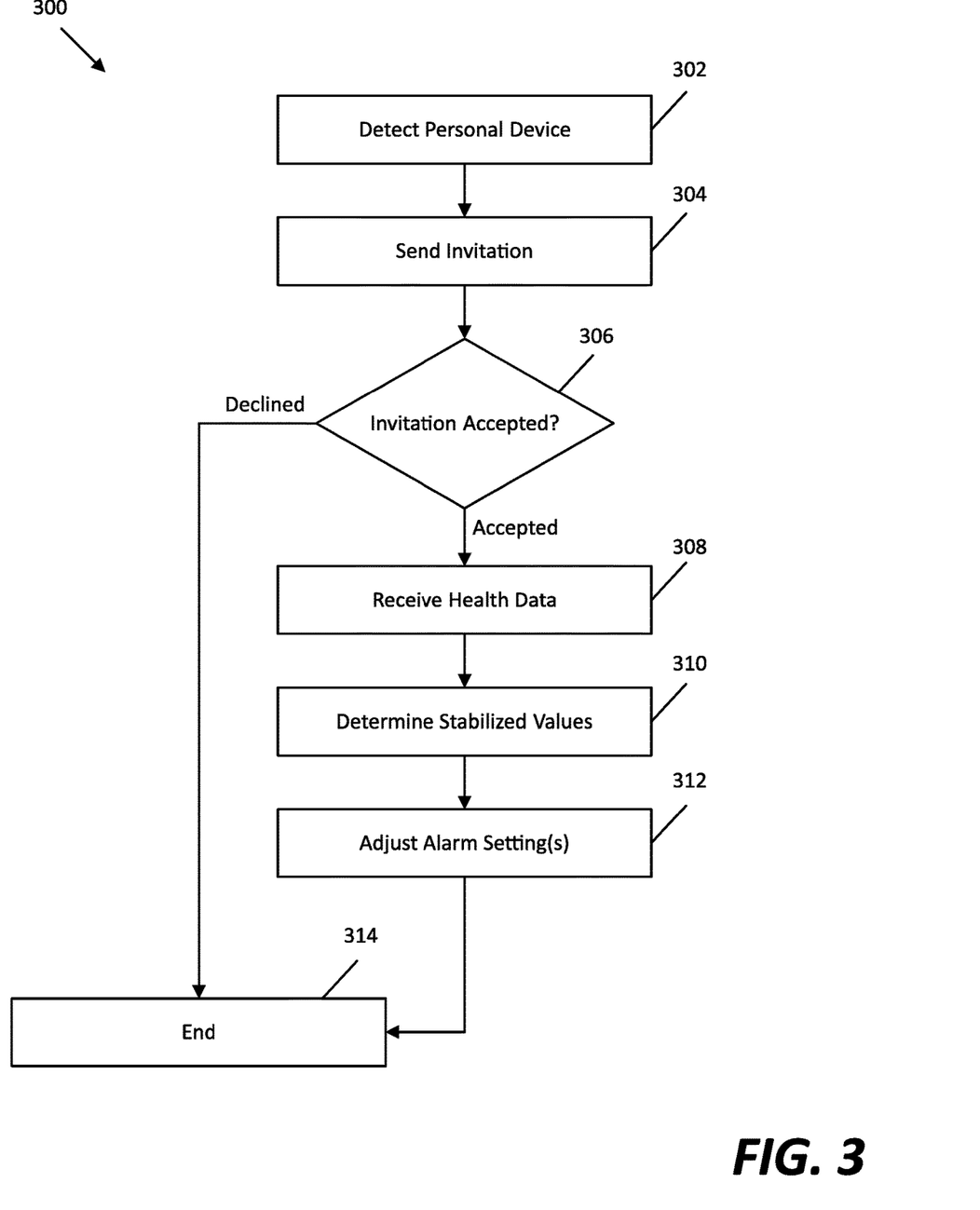
FIG. 3 illustrates an example of a method for monitoring a patient in a healthcare facility that can be performed by the monitor device of FIG. 1.

FIG. 3 illustrates an example of a method 300 for monitoring a patient in a healthcare facility. The method 300 can be performed by the monitor device 104 to adjust one or more alarm settings on the monitor device 104 to mitigate false alarms. More specifically, the method 300 can be performed by the monitor device 104 to personalize the one or more alarm settings for the patient P based on health data obtained from a personal device of the patient P.

As shown in FIG. 3, the method 300 includes an operation 302 of detecting a personal device 136 of the patient P such as the mobile device 138 or the fitness tracker 140. In some examples, the personal device 136 is detected when in close proximity to the monitor device 104 such as when both are inside the area 10. In some examples, the personal device 136 is detected via Bluetooth, Wi-Fi, ultra-wideband (UWB), and similar types of wireless protocols.

Next, the method 300 includes an operation 304 of sending an invitation to connect to the personal device 136. The invitation to connect can be sent via Bluetooth, Wi-Fi, ultra-wideband (UWB), and similar types of wireless communications protocols.

Next, the method 300 includes an operation 306 of determining whether the invitation to connect is accepted or declined. In some instances, the invitation to connect is accepted by the patient P using the personal device 136, and the acceptance is sent to the monitor device 104. For example, a notification can be generated on a touchscreen display of the personal device 136 that allows the patient P to accept or decline the invitation to connect with the monitor device 104.

In some instances, such as when the patient P is unconscious, operation 306 of determining whether the invitation to connect is accepted is based on a setting stored on the personal device 136. For example, prior to admission to the area 10, the patient P can adjust a privacy setting on the personal device 136 to share health data that is stored on the personal device 136 or that is otherwise accessible by the personal device 136 with the healthcare facility. When the privacy setting on the personal device 136 indicates that the patient P gives consent to share their health data with the healthcare facility, operation 306 determines that the invitation to connect is accepted. Otherwise, when the privacy setting on the personal device 136 indicates that the patient P does not give consent to share their health data with the healthcare facility, operation 306 determines that the invitation to connect is declined.

In further examples, determining whether the invitation to connect is accepted is based on a medical record of the patient. For example, the electronic medical record 204 of the patient P stored in the EMR system 202 (see FIG. 1) can include the patient P's preferences for sharing their health data on their personal devices with the healthcare facility. When the preferences indicate that the patient P gives consent to share their health data on their personal devices, operation 306 determines that the invitation to connect is accepted. Otherwise, when the preferences indicate that the patient P does not give consent to share their health data on their personal devices, operation 306 determines that the invitation to connect is declined.

In some examples, the method 300 can include an operation of displaying a notification on the monitor device 104 (e.g., on the display device 114) that identifies the personal device 136, and that includes a request for a clinician to accept or decline the invitation to connect the monitor device 104 to the personal device 136. In some instances, the notification is displayed on the display device 114 before the invitation to connect (e.g., operation 304) is sent to the personal device 136. When the clinician accepts the invitation to connect the monitor device 104 to the personal device 136, the method 300 proceeds to operation 304. Otherwise, when the clinician declines the invitation to connect the monitor device 104 to the personal device 136, the method 300 terminates at operation 314.

In some instances, the notification is displayed on the display device 114 after the invitation to connect (e.g., operation 304) is sent to the personal device 136, and before the method proceeds to an operation 308. In such instances, when the clinician accepts the invitation to connect the monitor device 104 to the personal device 136, the method 300 proceeds to operation 308. Otherwise, when the clinician declines the invitation to connect the monitor device 104 to the personal device 136, the method 300 terminates at operation 314.

Next, the method 300 includes an operation 308 of receiving health data from the personal device 136 (i.e., when the invitation to connect is determined as "accepted" in operation 306). The health data can include patient motion data and physiological variable data. Examples of the physiological variable data can include one or more physiological variables that are continuously monitored by the personal device 136 such as heart rate, electrocardiogram (ECG), blood oxygen saturation (SpO2), respiration rate, temperature, and the like. The physiological variable data can further include non-continuous variables including one or more of blood glucose level, systolic and diastolic blood pressure, and weight that can be acquired from one or more of the personal healthcare devices 142 that sync with the mobile device 138.

Next, the method 300 includes an operation 310 of determining stabilized values for one or more physiological variables of the patient P based on the health data received in operation 308. In some examples, operation 310 includes parsing the health data to determine stabilized values for one or more physiological variables of the patient P. For example, operation 310 can include filtering the physiological variable data based on the patient motion data such that only physiological variable data recorded when the patient P was in a stabilized state (e.g., was not moving) is used to calculate the stabilized values. The stabilized state can include when the patient P was resting (e.g., sitting or laying down) similar to how the patient P is sitting or laying down on the patient support system 102 shown in FIG. 1.

In some examples, the personal device 136 filters the physiological variable data based on the patient motion data prior to the monitor device 104 receiving the health data from the personal device 136. For example, the mobile device 138 or fitness tracker 140 can determine a resting heart rate of the patient P such that the monitor device 104 does not need to parse the health data from the mobile device 138 or fitness tracker 140 to determine the resting heart rate.

In other examples, the health data includes raw physiological variable data and raw patient motion data that are each respectively time stamped. In such examples, the monitor device 104 filters the raw physiological variable data to remove data based on the time stamps indicating when the patient P was moving (e.g., when the patient P was not in a stabilized state).

Operation 310 can determine a stabilized heart rate, a stabilized electrocardiogram (ECG), a stabilized blood oxygen saturation (SpO2), a stabilized respiration rate, and a stabilized temperature of the patient P. Operation 310 can also determine a stabilized blood glucose level, stabilized systolic and diastolic blood pressure, and stabilized weight of the patient P. In some instances, these stabilized values can be calibrated to improve accuracy.

Figure 4:
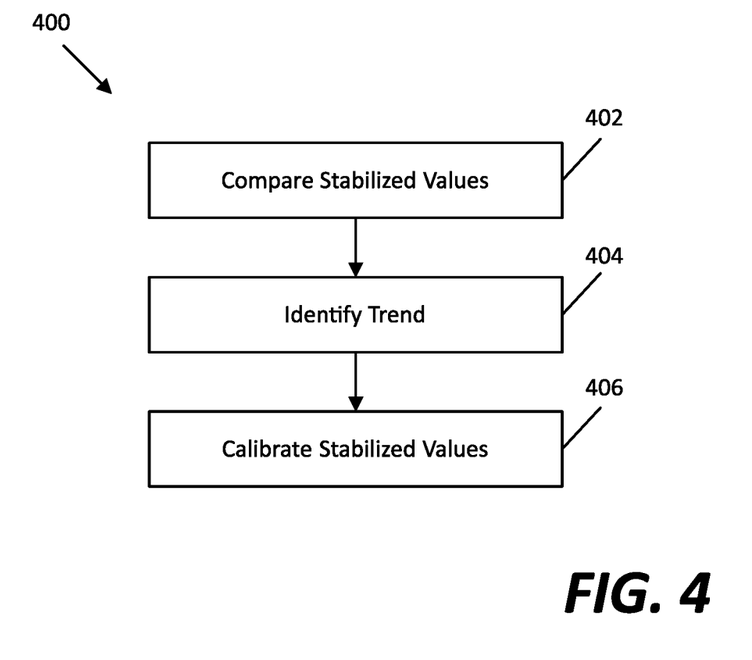
FIG. 4 illustrates an example of a method of calibrating stabilized values for one or more physiological variables determined during performance of the method of FIG. 3.

FIG. 4 illustrates an example of a method 400 of calibrating the stabilized values determined from operation 310. In some instances, the method 400 is performed a predetermined period of time after the patient P has been admitted to the area 10 to allow the patient P to stabilize following an intervention and while resting on the patient support system 102.

As shown in FIG. 4, the method 400 includes an operation 402 of comparing the stabilized values determined from operation 310 to data sensed from one or more of the source devices connected to the monitor device 104 such as the patient support system 102, the motion sensor 106, and the one or more physiological sensors 108 (see FIGS. 1 and 2).

Next, the method 400 includes an operation 404 of identifying a trend based on the comparison of the stabilized values to the data sensed from one or more of the source devices connected to the monitor device 104. For example, operation 404 can identify a trend that the stabilized values are consistently lower by X amount than the data sensed from one or more of the source devices connected to the monitor device 104. As another example, operation 404 can identify a trend that the stabilized values are consistently higher by X amount than the data sensed from one or more of the source devices connected to the monitor device 104.

Next, the method 400 includes an operation 406 of calibrating the stabilized values based on the trend identified from operation 404. For example, when a trend identifies that the stabilized values are consistently lower than the data sensed from one or more of the source devices connected to the monitor device 104, operation 406 can include increasing the stabilized values by X amount. As another example, when a trend identifies that the stabilized values are consistently higher than the data sensed from one or more of the source devices connected to the monitor device 104, operation 406 can include decreasing the stabilized values by X amount.

In some examples, the trends identified in operation 404 and/or the calibration performed in operation 406 are stored in the memory device 124 of the monitor device 104 for future reference and use. For example, when the monitor device 104 connects to a new personal device that belongs to a different patient, and when the new personal device is the same or is substantially similar to the personal device 136, the monitor device 104 can use the trends identified in operation 404 and/or the calibration performed in operation 406 to calibrate the stabilized values acquired from the new personal device. In this manner, the monitor device 104 can learn from prior connections the accuracy of physiological variable data acquired from various types of personal devices, and calibrate the data appropriately.

Referring back to FIG. 3, the method 300 includes an operation 312 of adjusting one or more alarm settings on the monitor device 104 based on the stabilized values determined from operation 310. The one or more alarm settings are personalized for the patient P based on the stabilized values determined from the health data acquired from the personal device 136.

Operation 312 can include increasing or decreasing an upper alarm limit based on a stabilized value, and increasing or decreasing a lower alarm limit based on the stabilized value. For example, when a stabilized value determined for blood pressure indicates that the patient P has high blood pressure when resting and under normal conditions, the upper and lower limits of a blood pressure alarm can be increased. As another example, when a stabilized value determined for heart rate indicates that the patient P has a low resting heart rate, the upper and lower limits of a heart rate alarm can be lowered. Additional examples are contemplated.

Operation 312 can also include setting a target value based on the stabilized values for one or more physiological variables following a treatment or intervention. For example, a target value for blood pressure after a blood pressure medication is administered to the patient P can be set to match a stabilized value determined for the patient P's blood pressure.

Operation 312 can also include determining a motion profile for the patient P based on the health data received from the personal device. The motion profile can be used to estimate changes in sensed physiological variables based on patient motion. For example, the motion profile can be used to estimate that the heart rate of the patient P increases by X amount when the patient leaves the patient support system 102 to use the restroom. Operation 312 can further include determining a motion weighted alarm delay based on the motion profile.

The various embodiments described above are provided by way of illustration only and should not be construed to be limiting in any way. Various modifications can be made to the embodiments described above without departing from the true spirit and scope of the disclosure.

What is claimed is:

1. A device for monitoring a patient, comprising:
at least one processing device; and
a memory device storing instructions which, when executed by the at least one processing device, cause the device to:
   detect a personal device of the patient;
   send an invitation to connect to the personal device;
   receive health data from the personal device when the invitation is accepted;
   determine stabilized values for one or more physiological variables of the patient based on the health data; and
   adjust one or more alarm settings based on the stabilized values, wherein adjust the one or more alarm settings includes determining a motion weighted alarm delay based on the health data.

2. The device of claim 1, wherein acceptance of the invitation is received from the patient using the personal device.

3. The device of claim 1, wherein acceptance of the invitation is received from a setting stored on the personal device.

4. The device of claim 1, wherein acceptance of the invitation is received from a medical record of the patient.

5. The device of claim 1, wherein the instructions, when executed by the at least one processing device, further cause the device to display a notification requesting a clinician to accept the invitation to connect the device to the personal device.

6. The device of claim 1, wherein adjust the one or more alarm settings includes increasing or decreasing an upper alarm limit, and increasing or decreasing a lower alarm limit.

7. The device of claim 1, wherein adjust the one or more alarm settings includes setting a target value for the one or more physiological variables following a treatment or intervention.

8. The device of claim 1, wherein the instructions, when executed by the at least one processing device, further cause the device to calibrate the stabilized values by comparing the stabilized values to data captured by one or more sensors connected to the device, identifying a trend based on the comparing, and calibrating the stabilized values based on the trend.

9. The device of claim 1, wherein the stabilized values include one or more of an electrocardiogram (ECG), a heart rate, a blood oxygen saturation (SpO2), a respiration rate, a temperature, a motion profile, a blood pressure, a blood glucose level, and weight.

10. A method for monitoring a patient, the method comprising:
   detecting a personal device of the patient;
   sending an invitation to connect to the personal device;
   receiving health data from the personal device when the invitation is accepted;
   determining stabilized values for one or more physiological variables of the patient based on the health data;
   adjusting one or more alarm settings based on the stabilized values;
   determining a motion profile for the patient based on the health data received from the personal device, wherein the motion profile estimates changes in the one or more physiological variables based on patient motion; and
   determining a motion weighted alarm delay based on the motion profile.

11. The method of claim 10, wherein adjusting the one or more alarm settings includes increasing or decreasing an upper alarm limit, and increasing or decreasing a lower alarm limit.

12. The method of claim 10, wherein adjusting the one or more alarm settings includes setting a target value for the one or more physiological variables following a treatment or intervention.

13. A non-transitory computer readable storage medium storing instructions, which when executed by at least one processing device, cause the at least one processing device to:
- detect a personal device of a patient;
- send an invitation to connect to the personal device;
- when the invitation is accepted, receive health data from the personal device;
- determine stabilized values for one or more physiological variables of the patient based on the health data;
- adjust one or more alarm settings based on the stabilized values;
- determine a motion profile for the patient based on the health data received from the personal device, wherein the motion profile estimates changes in the one or more physiological variables based on patient motion; and
- determine a motion weighted alarm delay based on the motion profile.

14. The non-transitory computer readable storage medium of claim 13, wherein adjust the one or more alarm settings includes increasing or decreasing an upper alarm limit, and increasing or decreasing a lower alarm limit.

15. The non-transitory computer readable storage medium of claim 13, wherein adjust the one or more alarm settings includes setting a target value for the one or more physiological variables following a treatment or intervention.

* * * * *